(12) United States Patent
Chandran et al.

(10) Patent No.: US 10,842,683 B2
(45) Date of Patent: Nov. 24, 2020

(54) FACIAL PADS FOR EXFOLIATION

(71) Applicant: Suprem Enterprises, Coimbatore (IN)

(72) Inventors: Prashanth Chandran, Coimbatore (IN); Pradeep Subramaniam, Coimbatore (IN); Balachandar Devarajan, Coimbatore (IN)

(73) Assignee: Suprem Enterprises, Coimbatore (IN)

( * ) Notice: Subject to any disclaimer, the term of this patent is extended or adjusted under 35 U.S.C. 154(b) by 153 days.

(21) Appl. No.: 15/964,140

(22) Filed: Apr. 27, 2018

(65) Prior Publication Data
US 2019/0105204 A1 Apr. 11, 2019

(51) Int. Cl.
| | |
|---|---|
| A61F 13/15 | (2006.01) |
| A61H 7/00 | (2006.01) |
| A47K 7/03 | (2006.01) |
| A61F 13/511 | (2006.01) |
| A61F 13/12 | (2006.01) |
| A45D 44/00 | (2006.01) |
| A61F 13/36 | (2006.01) |
| A47K 7/02 | (2006.01) |

(52) U.S. Cl.
CPC ........ *A61F 13/15252* (2013.01); *A45D 44/00* (2013.01); *A47K 7/02* (2013.01); *A47K 7/03* (2013.01); *A61F 13/122* (2013.01); *A61F 13/36* (2013.01); *A61F 13/51104* (2013.01); *A61F 13/51113* (2013.01); *A61H 7/003* (2013.01); *A45D 2200/1018* (2013.01); *A45D 2200/1054* (2013.01)

(58) Field of Classification Search
CPC .. A61F 13/15252; A61F 13/122; A61F 13/36; A61F 13/51104; A61F 13/51113; A61F 13/12; A61F 13/511; A45D 44/00; A45D 2200/1018; A45D 2200/1054; A47K 7/02; A47K 7/03; A47K 7/028; A61H 7/003; A61H 7/00; A61H 7/03; A47L 13/46; A47L 13/16; A47L 13/15; A63B 57/0087
See application file for complete search history.

(56) References Cited

U.S. PATENT DOCUMENTS

| | | | |
|---|---|---|---|
| 3,317,367 A * | 5/1967 | Koller ..................... | B29C 70/12 428/92 |
| 5,439,487 A * | 8/1995 | Stanitzok ................. | A46B 5/04 15/227 |
| 5,671,498 A | 9/1997 | Martin et al. | |

(Continued)

*Primary Examiner* — Robert J Scruggs
(74) *Attorney, Agent, or Firm* — Convergence Intellectual Property Law P.C.; Jonathan Garfinkel

(57) ABSTRACT

Biodegradable facial pads for exfoliation purposes are disclosed. The facial pad includes a top layer and a bottom layer made of a hydro-entangled, non-woven fibrous material. A coarse fabric material that may have undulations to provide exfoliating effect is sandwiched between the top layer and the bottom layer. The coarse fabric layer is configured to provide stiffness to the pads so as to aid and facilitate exfoliation. The top layer, bottom layer and the coarse material layer are pinched together along the edges to form an exfoliating pad of specified weight. The top layer is configured to overlay the coarse fabric layer to incorporate the undulations in the coarse fabric layer. This may form exfoliating peaks and absorbent cotton valleys that are suitable for removal of dead cells from the skin when used for exfoliating purposes.

17 Claims, 2 Drawing Sheets

(56) References Cited

U.S. PATENT DOCUMENTS

| | | | |
|---|---|---|---|
| 5,849,647 A | 12/1998 | Neveu et al. | |
| 6,998,360 B1 | 2/2006 | Picard | |
| 9,609,983 B2 * | 4/2017 | McCarthy | A47K 7/02 |
| 2002/0087167 A1 * | 7/2002 | Winitsky | A61B 17/32 |
| | | | 606/131 |
| 2004/0176002 A1 * | 9/2004 | Siegwart | A61Q 19/00 |
| | | | 442/35 |
| 2007/0082032 A1 * | 4/2007 | Gregoire | B32B 3/30 |
| | | | 424/443 |
| 2011/0302733 A1 * | 12/2011 | Yuan | A47K 7/03 |
| | | | 15/104.93 |
| 2012/0237718 A1 * | 9/2012 | Weisman | D04H 3/011 |
| | | | 428/89 |
| 2014/0100589 A1 * | 4/2014 | Gordon | A45D 34/04 |
| | | | 606/131 |

\* cited by examiner

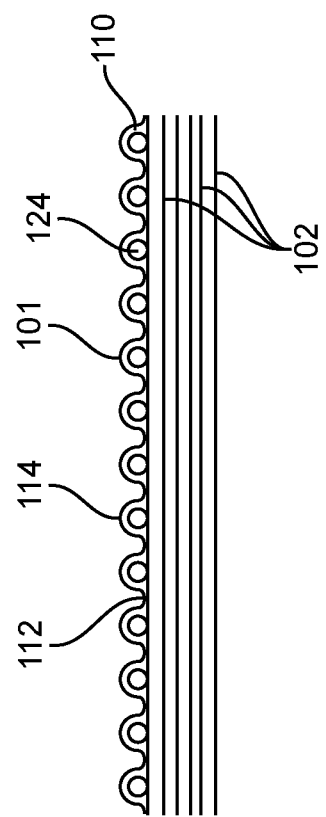
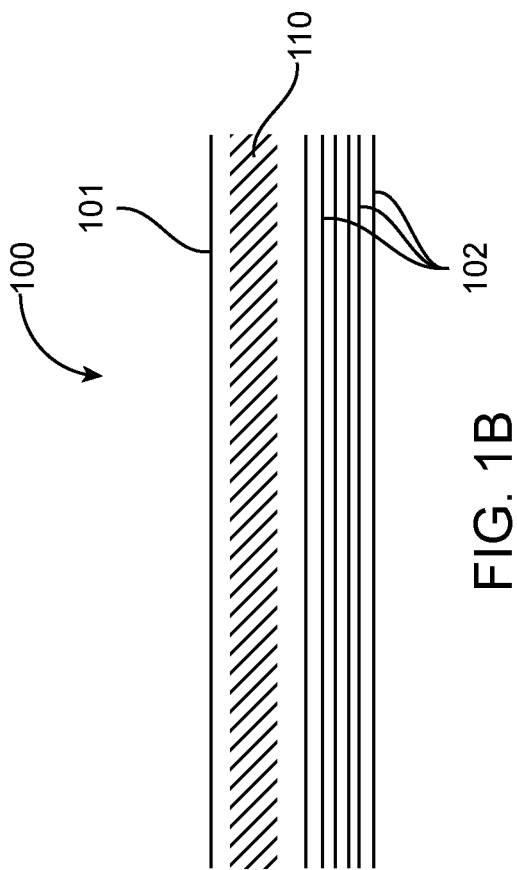
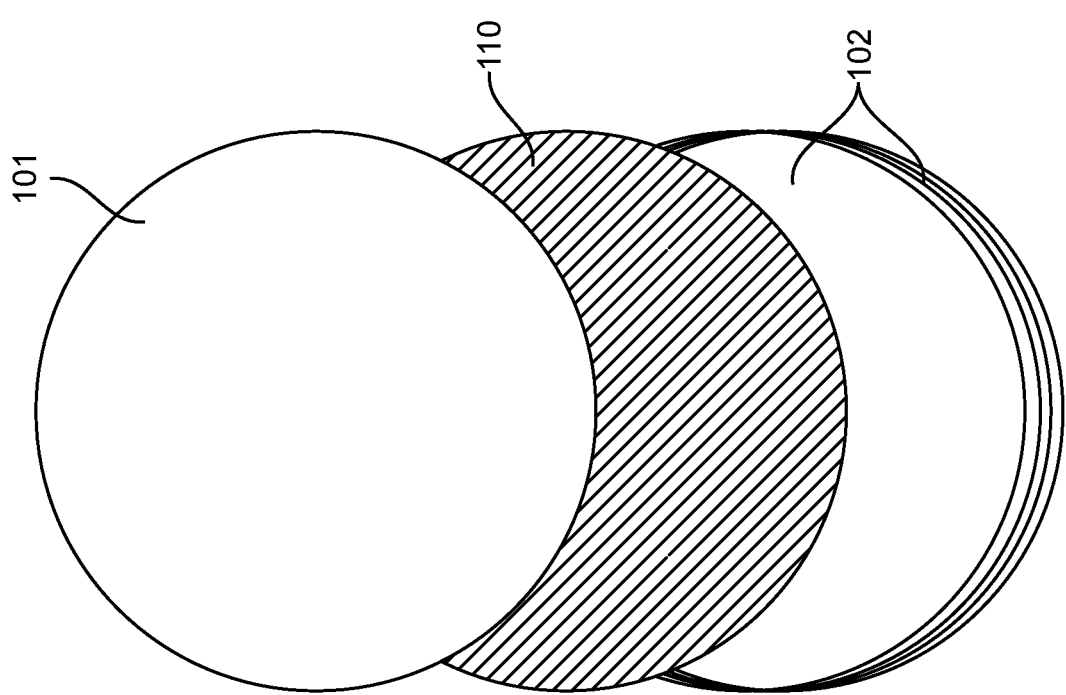

FACIAL PADS FOR EXFOLIATION

CROSS-REFERENCES TO RELATED APPLICATIONS

This application claims priority to Indian patent application No. 201741036199 filed on Oct. 11, 2017, the full disclosure of which is incorporated herein by reference.

FIELD OF THE INVENTION

The disclosure relates generally to facial pads and in particular to an exfoliating facial pad that uses a fabric material with undulations for exfoliation purposes.

DESCRIPTION OF THE RELATED ART

Cotton pads made of multi-layered non-woven fabric material are used for face cleansing, exfoliating, surface cleaning etc. These pads are multi-layered and use non-woven spun lace fabric. Exfoliating cotton discs presently available in the market have a rough surface which could damage the skin. For providing exfoliating effect various polymer materials are used that may be too harsh to the skin. However, use of polymer materials that are non-biodegradable may affect the disposability of the pads. U.S. Pat. No. 5,671,498 proposes a scrubbing device that may be adapted for use in manually dislodging unwanted scales from a target surface. U.S. Pat. No. 6,998,360 B1 discloses a hydrophilic cotton product comprising a soft surface and a scraping surface. U.S. Pat. No. 9,609,983B2 discloses a facial cleansing pad comprising a body constructed from a pliant fabric and having opposed first and second surfaces having two different knits. US20040176002A1 discusses a disposable skin cleansing implement. The U.S. Pat. No. 5,849,647A discloses a hydrophilic cotton lap. A product for exfoliating purpose is disclosed herein that overcomes many of the disadvantages discussed above.

SUMMARY OF THE INVENTION

The embodiments herein describe various aspects relating to exfoliating facial pads.

In one aspect, a facial pad for exfoliating purposes is included. The facial pad has a predetermined specific weight. It is made of a top layer including a material layer of a first fabric weight; a bottom layer including a material layer of a second fabric weight, the top and bottom layers comprising hydroentangled, non-woven fibrous material; and a coarse fabric material of a third fabric weight sandwiched between the top layer and the bottom layer, the coarse fabric material including undulations of exfoliating peaks and absorbent valleys and configured to provide a soft abrasive effect when overlaid with the top layer. The top layer, bottom layer, and the coarse fabric material layer are pinched together along the edges to form an exfoliating pad of predetermined specific weight and stiffness characteristics.

In one aspect, the first fabric weight of the top layer is 100 to 300 g per square meter. In another aspect, the fabric weight of the bottom layer is 100 to 300 g per square meter. In yet another aspect, the fabric weight of the coarse fabric layer is 30-60% of the weight of the exfoliating pad. In another aspect, the coarse fabric material is configured to strengthen the pad in the range from 20 N/5 cm to 650 N/5 cm. In another aspect, the top and bottom layers comprise absorbent cotton spun lace. In some aspects, the coarse fabric material is a woven cotton fabric material selected from one of broadcloth, canvas, or damask. In some aspects, the woven fabric material includes one of honeycomb, burlap, cardigan, diagonal or any other weave or knit texture. In some aspects, the coarse fabric material is of jute, hessian, banana fiber or any other natural fiber.

In some aspects, the coarse fabric material is of non-woven textured material comprising undulations. In one aspect, the top layer is either textured or smooth. In another aspect, the pad is circular, oval, rectangular or square shaped. In another aspect, the top layer, bottom layer, and the coarse fabric material layer are pinched together continuously along the edges. In another aspect, the pad is biodegradable. In various aspects, included in the facial pad is a composition configured to be released through the top layer upon contact with the subject's skin to aid in exfoliation, wherein the composition is coated on the coarse fabric material. In yet another aspect, the coarse fabric layer incorporates one or more substances selected from a seed, a seed husk, an extract thereof, or a combination thereof. In one aspect, the seed is millet, an oil seed, a cereal, or a combination thereof. In one aspect, the seed husk is coconut husk, paddy, wheat, oats husk, or a combination thereof. In one aspect, the coarse fabric layer comprises coarse fibers in a loose weave in the range of 5 to 40 yarns per inch in warp or weft directions, wherein warp fibers and weft fibers form a loose weave of 1 count to 30 count in English count units.

This and other aspects are disclosed herein.

BRIEF DESCRIPTION OF THE DRAWINGS

Present embodiments have other advantages and features which will be more readily apparent from the following detailed description and the appended claims, when taken in conjunction with the accompanying drawings, in which:

FIG. 1A shows exfoliating facial pad comprising a top layer, bottom layer and a coarse fabric material having undulations sandwiched between the top layer and bottom layer.

FIG. 1B illustrates cross section of the exfoliating pad with the layers in disassembled condition, FIG. 1C shows cross section of the exfoliating pad in the finished condition, showing undulations.

DETAILED DESCRIPTION OF THE EMBODIMENT

Figure 1E:
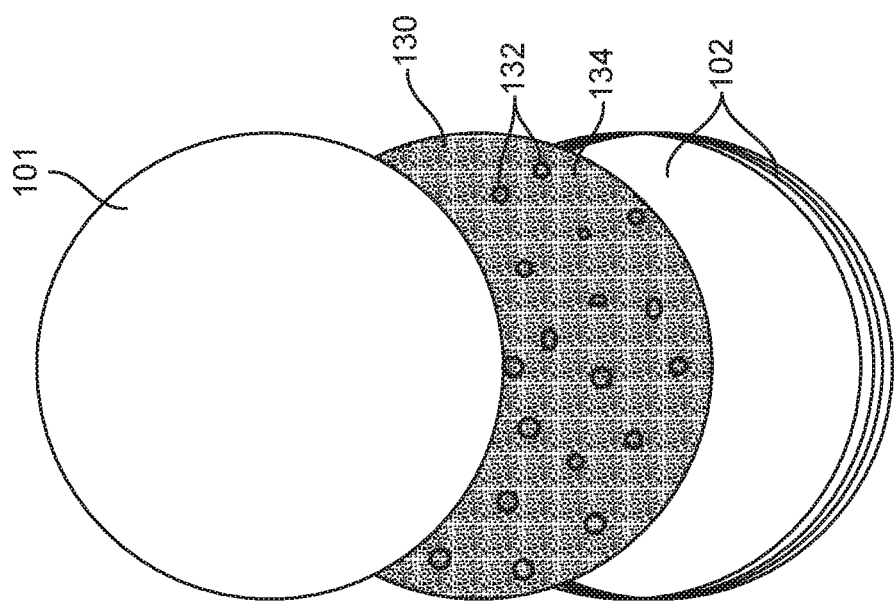
FIG. 1E illustrates use of plant seeds and extracts in the underlayer of exfoliating pads.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

Various embodiments propose a facial pad that is used for exfoliating purposes without the use of polymer or any non-biodegradable substances. The facial pad may have a specified weight and has exfoliating peaks and absorbent valleys incorporated by the overlaying of a coarse fabric material.

In various embodiments a facial pad 100 may be used for exfoliating purposes. The facial pad 100 as shown in FIG. 1A includes a top layer 101 and a bottom layer 102 made of a hydroentangled, non-woven fibrous material. The top layer 101 is configured to have a first weight and the bottom layer is configured to have a second weight. A coarse fabric material 110 that may include undulations to provide exfoliating effect is sandwiched between the top layer 101 and the bottom layer 102. In some embodiments, the top layer 101, bottom layer 102, and the coarse material layer 110 are pinched together along the edges to form an exfoliating pad. In some embodiments, the top layer 101 is configured to overlay the coarse fabric layer 110 to incorporate the undulations in the coarse fabric layer. The undulations in the coarse fabric layer may form exfoliating peaks 114 and absorbent valleys 112 as shown in FIG. 1C to provide the exfoliating pad with a soft abrasive effect. In some embodiments the exfoliating peaks of facial pad enables removal of dead cells from the skin when used for exfoliating purposes. In various embodiments, the facial pad 100 is configured to have a pre-configured strength or stiffness to ensure effective exfoliation. In various embodiments, the coarse fabric material 110 is configured to impart stiffness to the pad 100.

In one embodiment, the first fabric weight of the top layer in the facial pad is in the range of 15 to 300 g per square meter. In another embodiment, the first fabric weight is in the range of 100 to 300 g per square meter. In another embodiment the second fabric weight that includes the weight of the bottom layer in the facial pad is 15 to 300 g per square meter. In another embodiment, the second fabric weight is in the range of 100 to 300 g per square meter.

In various embodiments the non-woven fibrous material that is included in the top layer and the bottom layer of the facial pad is absorbent cotton spun lace material.

In some embodiments the coarse fabric material 110 that is sandwiched between the top layer and the bottom layer to provide an exfoliating effect in the facial pad may include a woven cotton material, or non-woven material of any natural or manmade fiber. In some embodiments the woven cotton material 110 or 120 may include broadcloth, canvas or damask weave. In some embodiments the coarse fabric may also include natural fibres such as jute, hemp, wool, silk, hessian, banana fiber or any other natural fiber or biodegradable manmade fibers such as polyglycolic acid, polylactic acid (PLA), polyhydroxyalkanoate (PHA), rayon, cellulose acetate, or mixtures thereof. In some embodiments the coarse fabric material may be a cotton net.

Figure 1D:
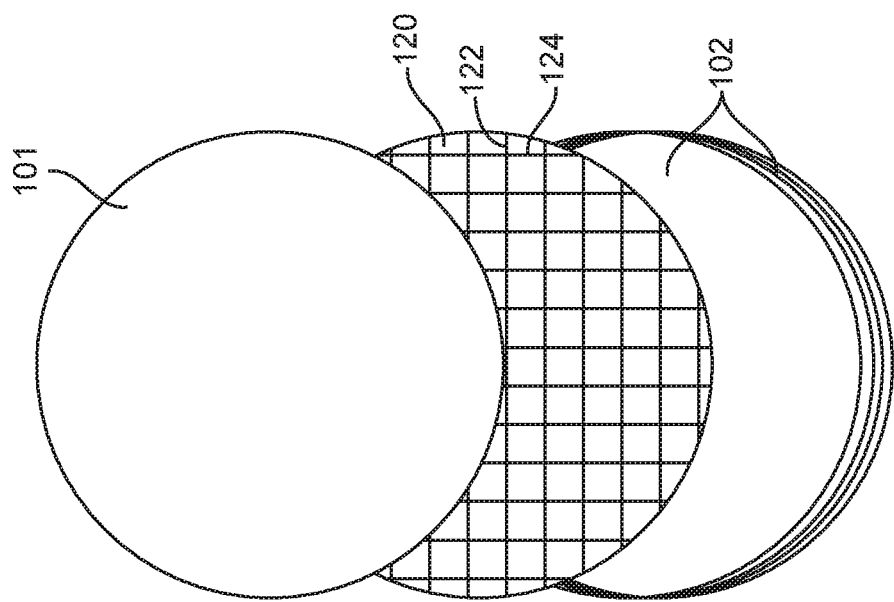
FIG. 1D illustrates use of coarse heavy weave underlayer to produce undulations.

In one embodiment, the coarse fabric material layer 120 is configured as illustrated in FIG. 1D and may comprise coarse fibers in a loose weave that may range from 5 to 40 yarns per inch in the warp or weft directions, wherein the warp fibers 122 and weft fibers 124 forming the loose weave are of 1 count to 30 count in English count units. In some embodiments the coarse fabric material may be of a third weight that is 30-60% of the weight of the exfoliating pad. In some embodiments the texture of the woven fabric material may include one of honeycomb, burlap, cardigan, diagonal or any other weave or knitting texture that may be coarse and that may provide an exfoliating effect on the top layer of the facial pad. In some embodiments the non-woven layer 110 of coarse fabric material may have undulations thereon, which may project through the top layer 101. The strength of the fabric in the embodiments illustrated in FIG. 1D may range from 20 N/5cm to 650 N/5 cm, as opposed to unreinforced pads that might have strength ranging from 0.1 to 10 N/5 cm. In some embodiments, the strength of the pads is improved by 2 to 65 times than that of the unreinforced pads. In various embodiments, the strength of the fabric is measured by subjecting the exfoliating pad to a tensile load.

In some embodiments, the coarse fabric material layer 130 is as shown in FIG. 1E and includes plant seeds, fragments or extract thereof 132 to provide the exfoliating effect. The plant seeds or seed fragments may in some embodiments range between 0.5 to 2 mm in size and may be used in quantity between 5 g to 50 g/sq. m. The coarse fabric material layer 130 in some embodiments incorporates one or more substances selected from natural seeds, or seed husk to provide abrasive quality or to provide undulations. The seeds may be one or more of millets such as ragi, jowar, bajra, sorghum, quinoa and the like or oil seeds like, jojoba, sunflower seed, sesame etc. The seeds may be cereals or broken cereals such as wheat, rice, etc. The seed husks may be coconut husk, paddy or wheat, or oats husk.

In some embodiments the layer 130 may additionally include a composition 134 suitable for external use in a subject. In one embodiment, the composition may include one or more substances extracted from jojoba seeds, or other seeds to aid exfoliation. In another embodiment, the composition is configured to be released through the top layer upon contact with the subject's skin for the desired exfoliation effect. In yet another embodiment, the composition is coated on the exfoliating peaks of the coarse fabric material.

In various embodiments the top layer that forms the point of contact of the facial pad with the skin may be textured or smooth. In some embodiments the facial pad may be of any convenient shape such as circular, oval, rectangular, square or other shape.

In various embodiments the top layer, bottom layer, and the exfoliating layer are pinched together continuously along the edges. The continuous edge closure may secure the facial pad from disintegrating when removed from its packing.

In various embodiments the facial pad is biodegradable in its entirety. The facial pads are soft, ecofriendly and gentle on the skin and are intended for exfoliation purposes. The absence of any extraneous constituent such as polymers or other synthetic material makes the pads totally biodegradable, and hence ecofriendly.

The facial pads disclosed herein when used for exfoliation purposes may remove dead cells from the skin effectively and may trap the removed dead cells in the absorbent cotton valley structure. The pads may also be used for make-up, eyeliner and lipstick removal applications.

While the invention has been disclosed with reference to certain embodiments, it will be understood by those skilled in the art that various changes may be made and equivalents may be substituted without departing from the scope of the invention. In addition, many modifications may be made to adapt to a particular situation or material the teachings of the invention without departing from its scope, which are as delineated in the claims to follow.

What is claimed is:

1. An exfoliating facial pad, comprising:
    a top layer of a first fabric weight;
    a bottom layer of a second fabric weight, the top and bottom layers comprising hydroentangled, non-woven fibrous material; and
    a coarse woven fabric layer of a third fabric weight sandwiched between the top layer and the bottom layer, the coarse fabric layer comprising undulations of exfoliating peaks and absorbent valleys and configured to strengthen the pad when sandwiched between the top layer and the bottom layer,
wherein the top layer, bottom layer, and the coarse fabric layer are pinched together along the edges and the undulations are formed on the top layer by the bonding of the top layer to the bottom layer through the coarse fabric layer, and wherein the coarse fabric layer comprises coarse fibers in a loose weave in the range of 5 to 40 yarns per inch in warp or weft directions, wherein warp fibers and weft fibers form a loose weave of 1 count to 30 count in English count units.

2. The facial pad of claim 1, wherein the first fabric weight is in the range of 15 to 300 g per square meter.

3. The facial pad of claim 1, wherein the second fabric weight is in the range of 15 to 300 g per square meter.

4. The facial pad of claim 1, wherein the coarse fabric layer strengthens the facial pad in the range from 20 N/5 cm to 650 N/5 cm.

5. The facial pad of claim 1, wherein the top and bottom layers comprise absorbent cotton spun lace.

6. The facial pad of claim 1, wherein the coarse woven fabric layer comprises a woven cotton fabric material selected from one of broadcloth, canvas, or damask.

7. The facial pad of claim 6, wherein the woven fabric material comprises one of honeycomb, burlap, cardigan, diagonal or any other weave or knit texture.

8. The facial pad of claim 1, wherein the coarse fabric layer comprises a material selected from jute, hessian, banana fiber or any other natural fiber.

9. The facial pad of claim 1, wherein the top layer is either textured or smooth.

10. The facial pad of claim 1, wherein the facial pad is circular, oval, rectangular or square shaped.

11. The facial pad of claim 1, wherein the top layer, bottom layer, and the coarse fabric layer are pinched together continuously along the edges.

12. The facial pad of claim 1, wherein the facial pad is biodegradable.

13. The facial pad of claim 1, further comprising a composition configured to be released through the top layer upon contact with a subject's skin to aid in exfoliation, wherein the composition is coated on the coarse fabric layer.

14. The facial pad of claim 1, wherein the coarse fabric layer incorporates a natural seed, a seed husk, or a combination thereof.

15. The facial pad of claim 14, wherein the natural seed is millet, an oil seed, a cereal, or a combination thereof.

16. The facial pad of claim 14, wherein the seed husk is coconut husk, paddy, wheat, oats husk, or a combination thereof.

17. The facial pad of claim 1, wherein the third fabric weight is in the range of 30-60% of the weight of the exfoliating pad.

* * * * *